(12) United States Patent
Blake, III

(10) Patent No.: US 6,869,435 B2
(45) Date of Patent: Mar. 22, 2005

(54) REPEATING MULTI-CLIP APPLIER

(76) Inventor: John W Blake, III, 77 Locust St., New Canaan, CT (US) 06840

( * ) Notice: Subject to any disclaimer, the term of this patent is extended or adjusted under 35 U.S.C. 154(b) by 40 days.

(21) Appl. No.: 10/051,513

(22) Filed: Jan. 17, 2002

(65) Prior Publication Data

US 2003/0135224 A1 Jul. 17, 2003

(51) Int. Cl.⁷ .............................................. A61B 17/04
(52) U.S. Cl. ....................................................... 606/143
(58) Field of Search ................................. 606/142, 143

(56) References Cited

U.S. PATENT DOCUMENTS

| | | | | |
|---|---|---|---|---|
| 4,425,915 A | * | 1/1984 | Ivanov ........................ | 606/143 |
| 4,430,997 A | * | 2/1984 | DiGiovanni et al. ......... | 606/143 |
| 4,850,355 A | * | 7/1989 | Brooks et al. ............... | 606/143 |
| 5,084,057 A | * | 1/1992 | Green et al. ................. | 606/142 |
| 5,104,395 A | * | 4/1992 | Thornton et al. ............ | 606/143 |
| 5,366,134 A | * | 11/1994 | Green et al. ............... | 227/176.1 |
| 5,403,327 A | * | 4/1995 | Thornton et al. ............ | 606/143 |
| 5,431,668 A | * | 7/1995 | Burbank et al. ............. | 606/143 |
| 5,484,095 A | * | 1/1996 | Green et al. .............. | 227/181.1 |
| 5,527,318 A | * | 6/1996 | McGarry ..................... | 606/139 |
| 5,527,326 A | * | 6/1996 | Hermann et al. ............ | 606/159 |
| 5,634,930 A | * | 6/1997 | Thornton et al. ............ | 606/143 |
| 6,171,316 B1 | * | 1/2001 | Kovac et al. ................ | 606/144 |

* cited by examiner

Primary Examiner—Gary Jackson
(74) Attorney, Agent, or Firm—Patrick J. Walsh

(57) ABSTRACT

An instrument for applying clips in surgery having an operating handle with operating components and a removable clip cartridge with clip applying mechanism. The handle operating components generate reciprocal linear motion imparted to the clip applying mechanism and accommodate rotation of the cartridge about a cartridge axis. An anti-backup mechanism constrains operating components to complete first and second strokes of reciprocal linear motion. The clip applying mechanism actuated by received reciprocal motion applies a clip in surgery, isolates the next clip, and prepares for loading the isolated clip into the jaws on a first stroke, and on the second stroke, opens the jaws and pushes the isolated clip into the open jaws.

16 Claims, 14 Drawing Sheets

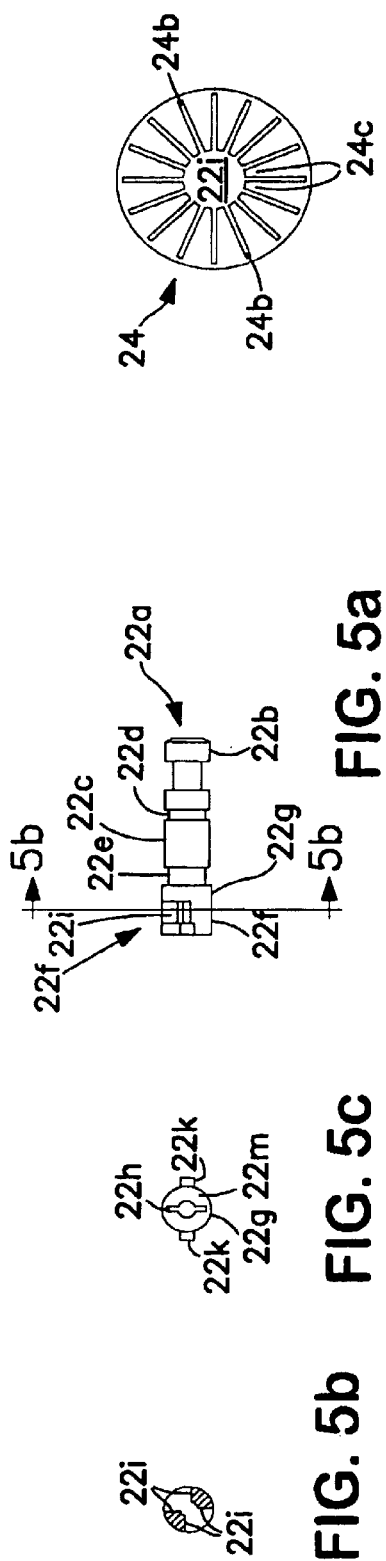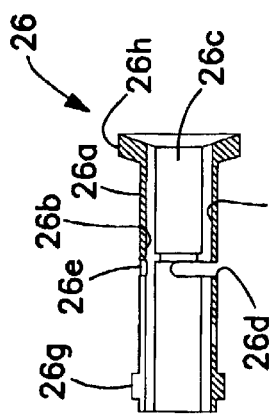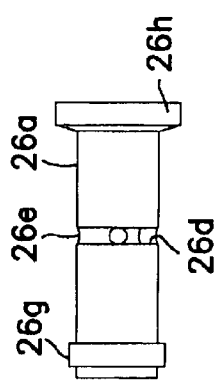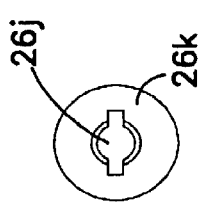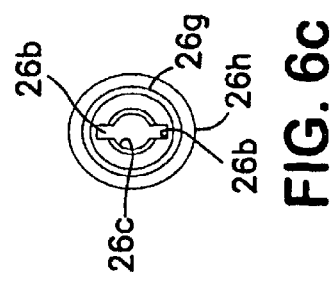

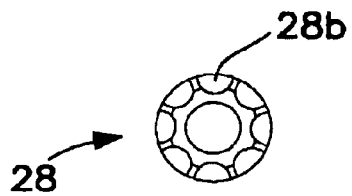
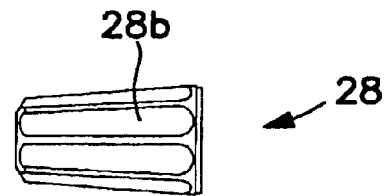
FIG. 8c  FIG. 8a
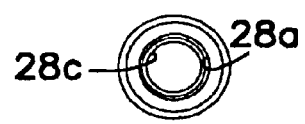
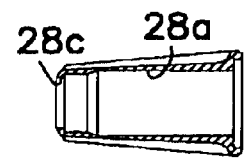
FIG. 8d  FIG. 8b

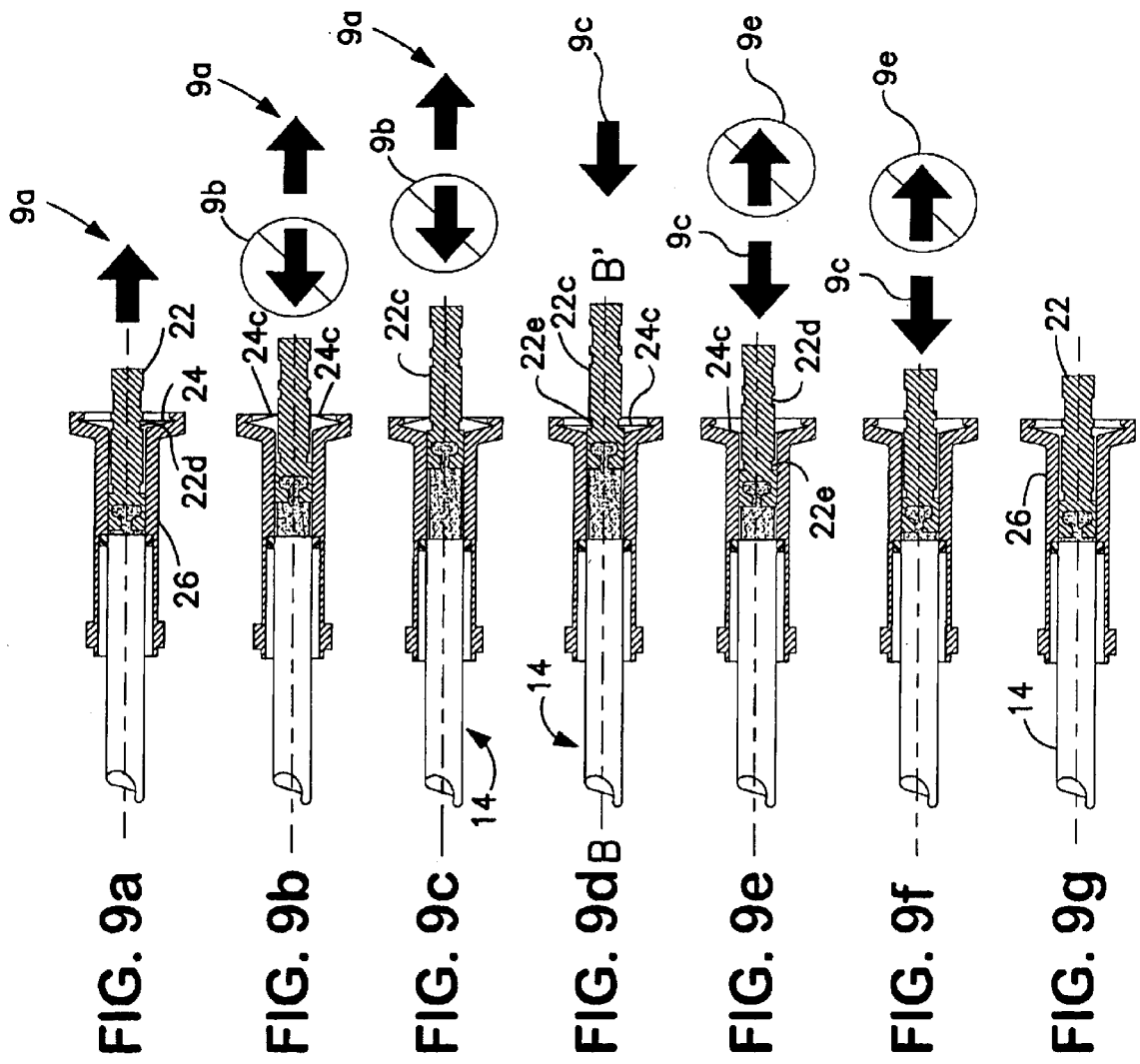

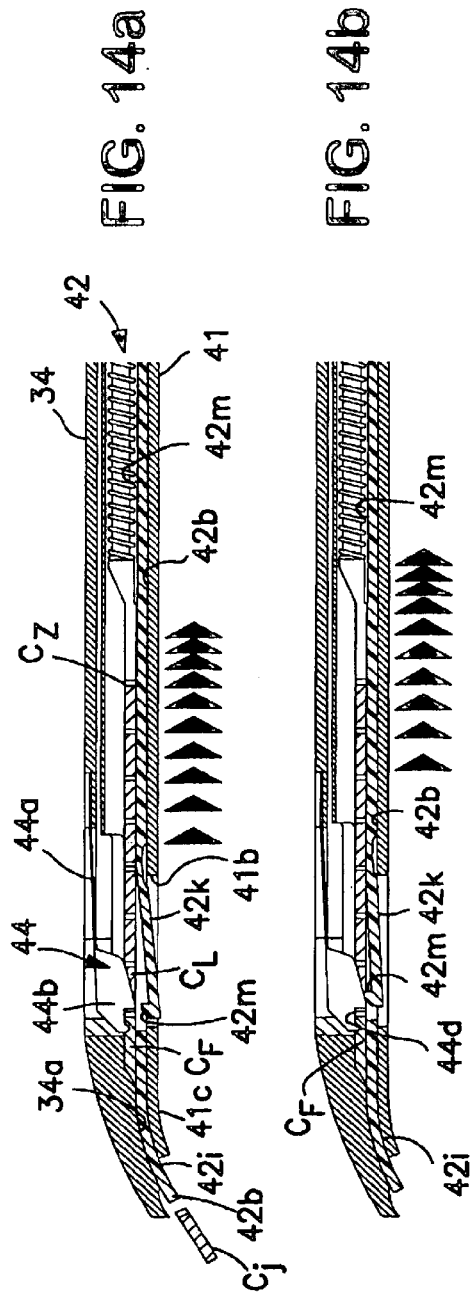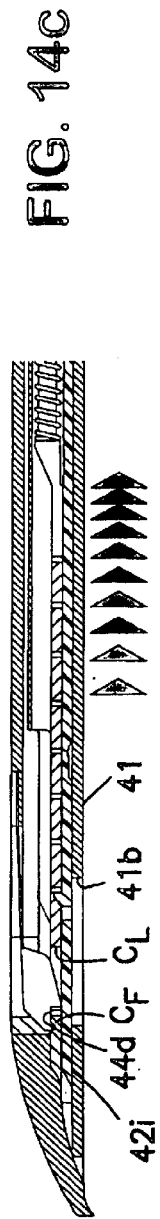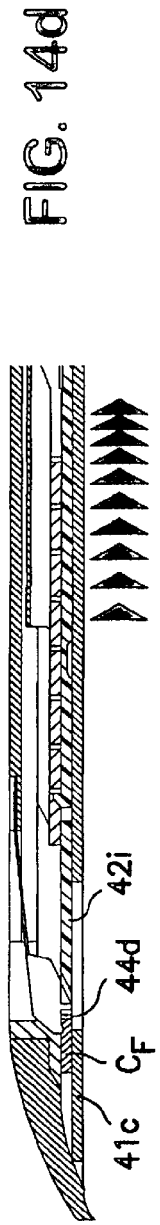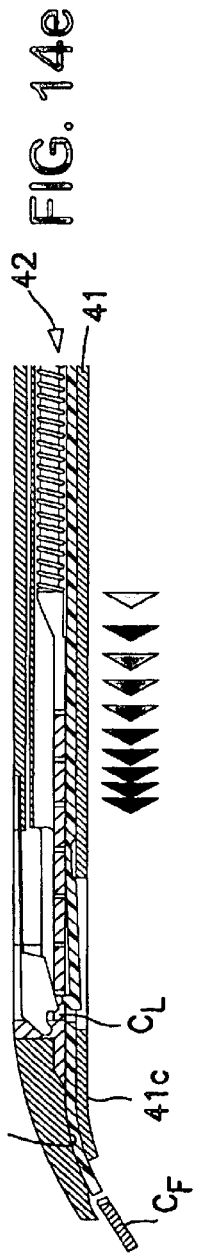
FIG. 14a
FIG. 14b
FIG. 14c
FIG. 14d
FIG. 14e

REPEATING MULTI-CLIP APPLIER

BACKGROUND OF THE INVENTION

The present invention relates to surgical clip appliers embodied as an instrument having a supply of clips for rapidly deploying several clips in closing severed blood vessels and other small fluid carrying ducts in surgical procedures. There are many different designs for surgical clip applicators for a variety of surgical procedures including both open surgery and laparoscopy in which a clipping appliance fits through a trocar tube into a body cavity where the clips are applied.

This invention comprises improvements in repeating multi-clip appliers of the kind described and claimed in my co-pending application Ser. No. 09/521,444 filed Mar. 7, 2000, now U.S. Pat. No. 6,423,079. A surgical clip applicator described in the co-pending application comprises an operating handle and clip applying mechanism having an operating cycle in which operating levers are squeezed together and released. In this operating cycle, a clip is applied in surgery and the clip applicator is reloaded with a single clip from a clip supply channel for clip application in the next cycle. The applicator provides a moveable clip supply channel containing a line of clips that are released seriatim. The supply channel integrates a clip pusher and an escapement or clip stop spring in a single unit.

Clip crimping jaws apply a clip with a rearward movement of a camming member thereby allowing the functions of clip loading and jaw closure to be coordinated and operated by a single sliding bar moving reciprocally to load and fire clips.

The clip actuating mechanism includes a combined actuating rod and in-line clip supply channel together with clip indexing mechanisms arranged so that with a squeeze of the operating levers, the actuating rod moves rearward in the appliance to apply a clip in surgery, capture the next in-line clip, index a line of clips rearward away from the clip jaws; and that with release of the operating levers, the jaws open, the next in-line clip is loaded into the jaws, the second next in-line clip is separated from the line, and the clip indexing movement is reset for the next cycle. The clip applicator includes a novel mechanism with minimal complexity especially suited for a disposable cartridge for fixed handle appliances.

A clip applicator of the co-pending application also employs low operating force without recoil, a clip counter, jaw lockout after the last clip and is adaptable for use as a quick snap-in disposable cartridge with a fixed non-disposable operating handle. An operating handle that provides linear reciprocating motion including scissors-type or pistol grip is used with that invention.

In practice, clip cartridges are ordinarily used a single time and discarded. Operating handles, on the other hand, may be disposed of after use with a single cartridge, may be used with a plurality of cartridges in a single surgical procedure and then discarded, or may be autoclaved after each surgical procedure and used over and over again.

This invention provides improvements for a repeating multi-clip applier having a simplified mechanism for applying clips which mechanism is suitable for the full spectrum of clip appliers including open surgery and laparoscopy. The applier mechanism is particularly adaptable to the disposable cartridge/fixed handle design. The simplified mechanism reduces tooling and assembly requirements, provides high operating reliability at lower product cost.

SUMMARY OF THE INVENTION

A preferred embodiment of repeating multi-clip applier according to the present invention comprises an instrument having an operating handle housing and a removable, fully rotatable and disposable clip applying cartridge. A full squeeze and release of operating handles applies a clip to a surgical site and reloads another clip into clip applying jaws of the instrument.

The operating handle housing preferably accommodates a pistol grip set of handles which provide linear reciprocating motion by means of a spring biased translator slide for actuating the clip applying mechanism within the cartridge. The operating handle housing includes a rotary thumb wheel hub and rotatable drum subassembly which receive the clip cartridge for 360° rotation about the cartridge axis and which link the cartridge clip applying mechanism to the translator slide.

The operating handle housing accommodates an anti-backup mechanism to prevent a partial pull and release of the operating handles. A well-known hazard with clip appliers is a condition of releasing a partially closed clip in a surgical site. This condition results when operating handles are given a partial pull or closing and then released. The partial pull crimps but does not close a clip located in the instrument jaws. When partially pulled handles of some older instruments are released, the instrument jaws re-open and the partially closed clip falls from the jaws into the surgical site. The present invention prevents occurrence of this condition by means of an anti-backup mechanism to ensure that when the appliance handles are pulled, the handles must be given a full pull to execute a complete cycle of the clip applier mechanism. If a partial pull of the appliance handles occurs, the anti-backup mechanism retains or holds the clip applier mechanism in fixed position without possibility of backup or reverse. The anti-backup "hold" is released simply by giving the handles a complete pull. When a partial pull occurs and the anti-backup mechanism holds the clip applying mechanism in place, the instrument jaws remain partially closed holding a partially closed clip thereby preventing the clip from falling into a surgical site. The anti-backup mechanism also functions in the opposite, or release, motion of operating handles. That is, the operating handles when being released are constrained by the anti-backup mechanism to undergo a full release motion. The anti-backup mechanism prevents partial release and re-pull of the trigger thereby to prevent double loading of a clip into the crimping jaws, a condition that would jam the instrument.

The clip applying mechanism includes a combined actuating rod and in-line clip supply cartridge together with clip advancing mechanisms arranged so that with a squeeze of the operating handle, the actuating rod moves rearward in the instrument to apply a clip in surgery, capture the next in-line clip, retain and move a line of clips rearward away from the clip jaws, and that with release of the operating levers, the jaws open, the next in-line clip is loaded into the jaws, the second next in-line clip is separated from the line, and the clip retaining means is reset for the next cycle.

The clip applying mechanism of the invention may include a flexible shaft interposed between operating handle and clip cartridge. The flexible shaft is capable of bending as desired up to 360° with respect to its handle as the clip cartridge maintains full operational clip applying integrity.

The clip applying cartridge according to the invention may be used with any kind of operating handle that can provide linear reciprocating motion to the actuating rod or puller bar of the cartridge clip applying mechanism. The clip applying cartridge may be used with a pistol grip operating handle as disclosed, a scissor type handle, or with a surgical robot such as used in a da Vinci™ surgical system.

Specific examples are included in the following description for purposes of clarity, but various details can be changed within the scope of the present invention.

OBJECTS OF THE INVENTION

An object of the invention is to provide a novel clip applicator with minimum complexity and with adaptability to a complete range of clip applicators including open and laproscopic surgery.

Another object of the invention is to provide a clip applicator adaptable for use with a replaceable cartridge.

Another object of the invention is to provide a clip applicator having an operating handle that provides anti-backup linear reciprocating motion and accommodates rotary motion of a clip applying cartridge.

Another object of the invention is to provide a clip applicator in which clip feed and applying mechanisms are driven by an actuator having a linear reciprocating motion generated by operating handles.

Another object of the invention is to provide a surgical clip applier with an anti-backup means to prevent release of partially closed clips at a surgical site.

Another object of the invention is to provide a surgical clip applier with clip applying cartridge rotatable through 360°.

Another object of the invention is to provide a surgical clip applier with a flexible shaft capable of bending as desired up to 360° interposed between clip applying cartridge and operating handles.

Another object of the invention is to provide a clip applying cartridge which can be used with various operating handle configurations including pistol grip, scissor type, and surgical robot.

Other and further objects of the invention will become apparent with an understanding of the following detailed description of the invention or upon employment of the invention in practice.

BRIEF DESCRIPTION OF THE DRAWING

A preferred embodiment of the invention has been chosen for detailed description to enable those having ordinary skill in the art to which the invention appertains to readily understand how to construct and use the invention and is shown in the accompanying drawing in which:

FIG. 5a is a side elevation of a rotary translator.

FIG. 5b is section view taken along line 5b—5b of FIG. 5a.

FIG. 5c is a front elevation of rotary translator.

FIG. 6a is a side elevation view of the rotary drum.

FIG. 6b is a longitudinal section view of the rotary drum of FIG. 6a.

FIG. 6c is an elevational view of the front face of the rotary drum of FIG. 6a.

FIG. 6d is an elevational view of the rear face of the rotary drum of FIG. 6a.

FIG. 7 is a front elevation of anti-backup disc.

FIG. 8a is a side elevation view of thumb wheel hub.

FIG. 8b is a longitudinal section view of the thumb wheel hub of FIG. 8a.

FIG. 8c is an elevational view of the the front face of the thumb wheel hub of FIG. 8a.

FIG. 8d is an elevational view of the the rear face of the thumb wheel hub of FIG. 8a.

FIGS. 9a–g are sequential views of anti-backup mechanism with disc in (a) rear groove, (b)&(c) between grooves, (d) in front groove, (e)&(f) between grooves, and (g) again in rear groove, and with arrows indicating directions of permitted and prevented movement of operating handle and cartridge mechanism.

FIGS. 14a, b, c, d and e are fragmentary section views of the sequence of (a) a clip loaded in the jaws ready to fire and clip fired, (b) next-in-line clip being detained, (c) line of clips in cartridge being indexed rearward, (d) next-in-line clip moved downward into loading position, and (e) next-in line-clip loaded into the jaws ready for firing.

DETAILED DESCRIPTION OF THE PREFERRED EMBODIMENT

Figure 1:
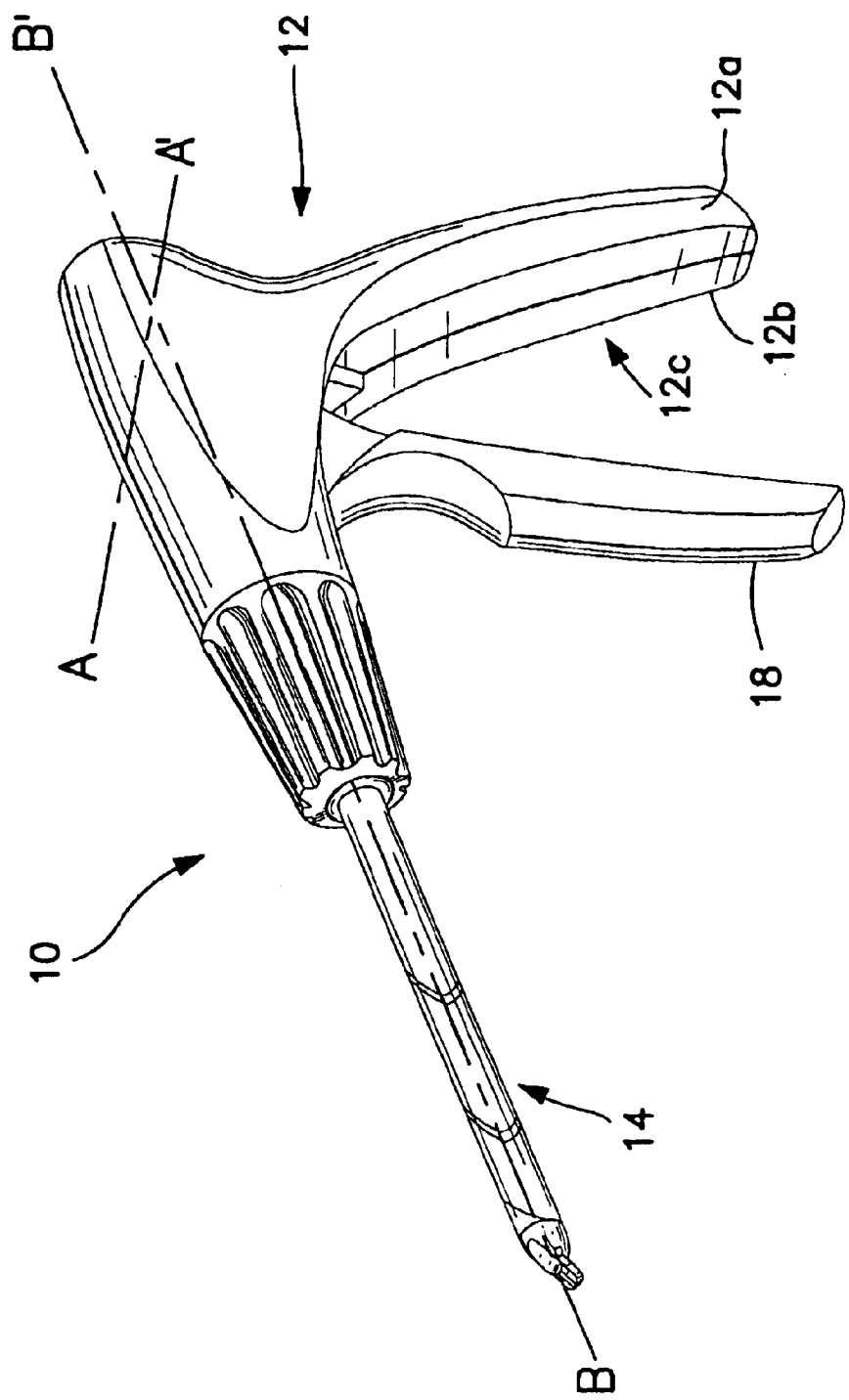
FIG. 1 is a perspective view of a preferred embodiment of surgical clip applicator according to the invention with location of A–A' and B–B' axes.

Referring to the drawing, a preferred embodiment of the repeating multi-clip applier 10 comprises operating handle housing 12 and clip applicator cartridge 14.

Figure 2:
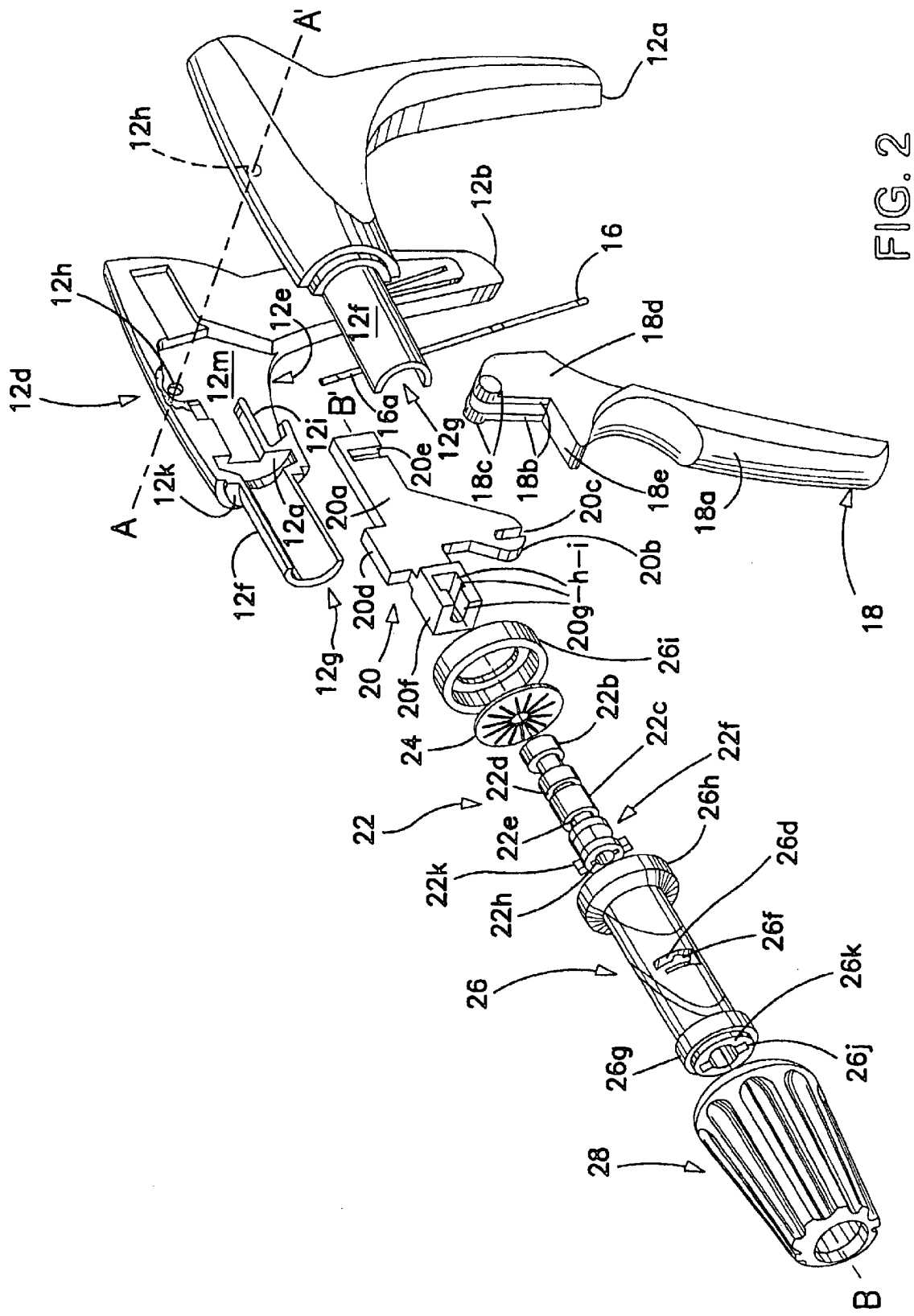
FIG. 2 is an exploded perspective view of the handle components of surgical clip applicator of FIG. 1 including handle subassembly locating trigger pivot A–A' axis, and subassembly of fixed translator, rotary translator, anti-backup mechanism, rotatable drum, and thumb wheel aligned on B–B' axis.

The operating handle housing 12 shown in FIGS. 1–4 comprises left 12a and right 12b handle members defining a depending grip 12c, a center section 12d defining a central chamber 12e, and a forward cylindrical portion 12f defining a forward chamber 12g. Preferably, the interior defining surfaces 12e, 12g of the right handle member shown in FIG. 2 are substantially the same as the corresponding interior surfaces of the left handle member. The handle members are joined along a mid-plane and together receive handle operating components within the central and forward chambers. The handle members define a depending pistol type grip which receives a bar spring 16 forming part of the applier mechanism.

A trigger 18 for actuating applier mechanisms is mounted on the housing for pivotal movement about axis A–A'. The trigger includes a depending grip portion 18a integral with upwardly extending arms 18b fitted with pivot pins 18c received in corresponding hubs 12h located within housing central chamber and defining the A–A' axis. The outer surfaces 18d of the trigger arms are in surface contact with the adjacent inner surfaces 12m of the housing central chamber so as to confine trigger movement to a smooth circular movement about axis A–A'.

The trigger has a forwardly projecting shoulder 18e for engaging a plate 12i affixed to the housing at the central chamber for the purpose of establishing the forward limit of travel of the trigger about axis A–A' under the force of the bar spring 16 acting through fixed translator 20.

The trigger when pulled transmits motion to the clip cartridge mechanism 14a (FIG. 11) through the intermediation of fixed translator slide 20 and a rotary translator 22. The trigger cooperates with the fixed translator slide 20 to provide reciprocal rectilinear motion of predetermined excursion along B–B' axis, and the fixed translator slide cooperates with the rotary translator 22 to transmit reciprocal rectilinear motion of predetermined excursion and to accommodate 360° rotation about the B–B' axis of the rotary translator. In this way, the actuating mechanism 14a of the clip cartridge receives reciprocating rectilinear motion of fixed excursion while the clip cartridge is free to rotate 360° in either direction about the applicator B–B' axis.

The fixed translator 20 functions as a slide which determines its contour. The fixed translator has an elongate body 20a with depending leg 20b having an open slot 20c defining a drive pin recess, an upper block 20d, a spring recess 20e, and an open front cage 20f. The fixed translator and the trigger form a subassembly with the translator located between the arms 18b of the trigger, and with the drive pin recess 20c fitted over a drive pin 18f (FIGS. 3, 4) positioned between the trigger arms. The location of the fixed translator between the upwardly extending arms of the trigger helps prevent the trigger arm pivot pins from popping out of their A–A' axis hubs 12h. When assembled with the operating handle housing, the fixed translator slides along central chamber surfaces 12m on either side of the trigger subassembly. The central chamber also accommodates the upper block 20d which in cooperation with the chamber walls limits forward and rearward movement of the trigger/fixed translator subassembly. The upper tip 16a of the bar spring fits into the spring recess 20e to provide a forward bias to the subassembly. So a pull of the trigger against the spring produces a circular trigger motion, i.e., a pivoting motion about axis A–A', which is received by the fixed translator as a rectilinear movement of excursion fixed by the interior contours of the central chamber and the upper block of the fixed translator. The drive pin recess 20c accommodates curvilinear movement of the trigger drive pin 18f and rectilinear movement of the translator. The front cage 20f of the fixed translator has an open front 20g, interior lip 20h, and open side 20i to receive and retain rotary translator 22.

The rotary translator 22 (FIGS. 2, 3 and 5) forms a subassembly with an anti-backup mechanism 24, a rotatable drum 26, and a thumb wheel hub 28 which subassembly interconnects the fixed translator 20 and the clip cartridge 14 for performing the functions of transmitting reciprocating rectilinear motion with a fixed excursion, accommodating rotary motion of the clip cartridge, enabling mounting and disconnecting of the clip cartridge from the operating handle, and providing an anti-backup capability for the operating handle and cartridge mechanism.

The rotary translator 22 (FIGS. 2, 5) comprises an elongate generally cylindrical shaft 22a with a rear flange 22b for connection to the fixed translator cage 20f so as to accommodate rectilinear motion of the rotary translator and fixed translator as a unit, and to accommodate rotary motion of the translator about the B–B' axis independent of the fixed translator. The center section 22c of the rotary translator shaft has spaced anti-backup grooves 22d, 22e with the distance between the grooves being approximately equal to the distance of reciprocating rectilinear motion of the fixed translator and, as becomes clear below, equal to the rectilinear excursion of the clip applicator mechanism. The intermediate cylindrical surface 22c of the rotary translator cooperates with an anti-backup disc 24 described more particularly next below. The rotary translator further includes a front end cage 22f for connection to the clip cartridge mechanism 14a. The front end cage is defined by a front flange 22g with a key hole 22h through its front face, a set of four interior, longitudinally extending shoulders 22i, and a pair of knobs 22k projecting radially from the flange rim. The rotary translator fits within a rotatable drum 26 (FIGS. 2, 6) which drum integrates subassembly components.

The rotary drum 26 is in the general form of a cylindrical sleeve 26a for orientation along the B–B' axis, with diametrically opposed interior grooves 26b extending the full length of the interior surface 26c of the sleeve, a pair of radially opposed slots 26d, 26e extending through the sleeve wall 26a, an integral wall spring 26f (FIG. 2) adjacent one of the slots 26d, a front end flange 26g, and an enlarged rear end flange 26h. The front flange includes a key hole 26j in front face 26k.

Figure 3:
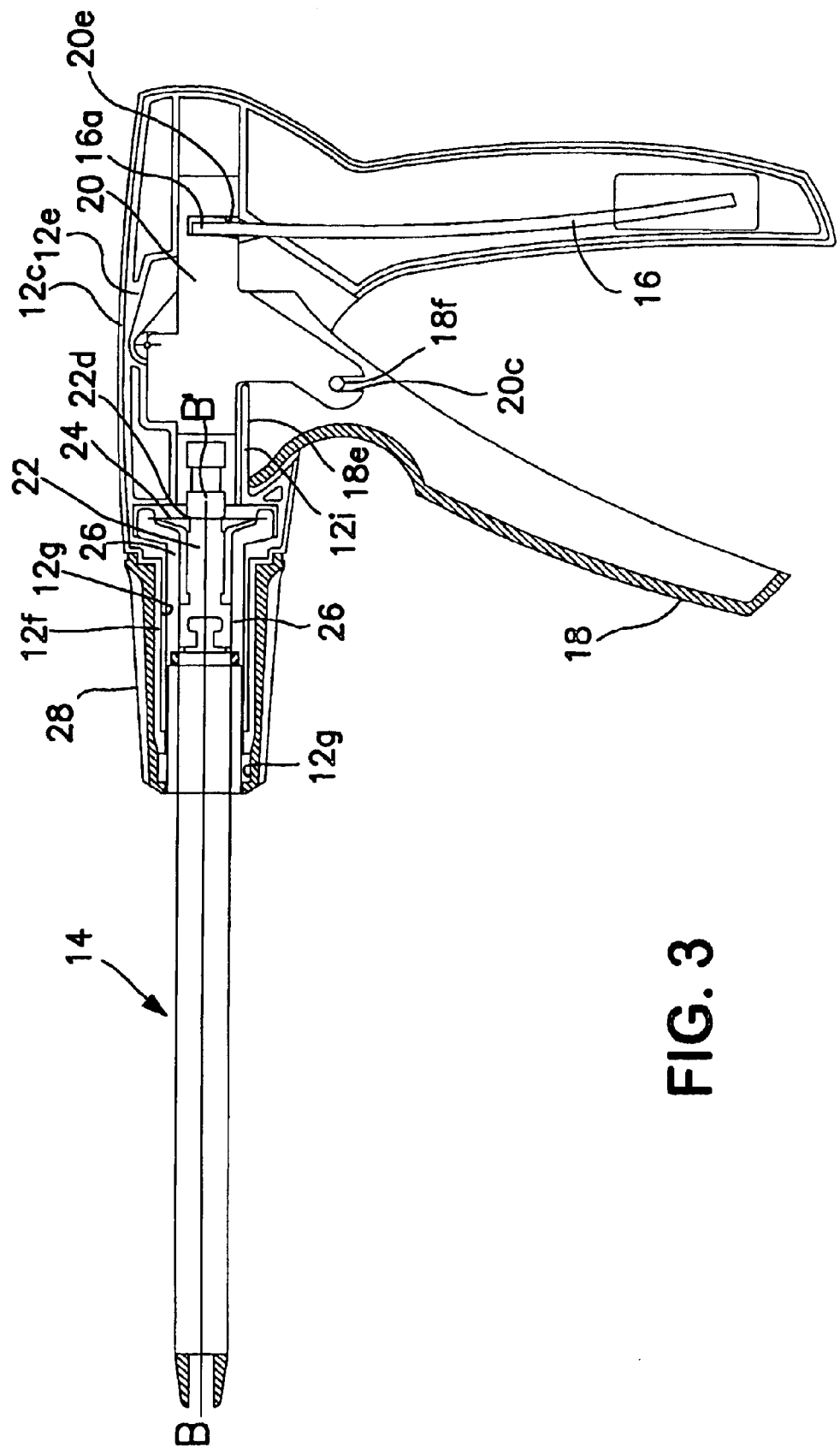
FIG. 3 is a side elevation view of the applicator of FIG. 1 with the operating handle housing partially in section and with handles in release position.
Figure 4:
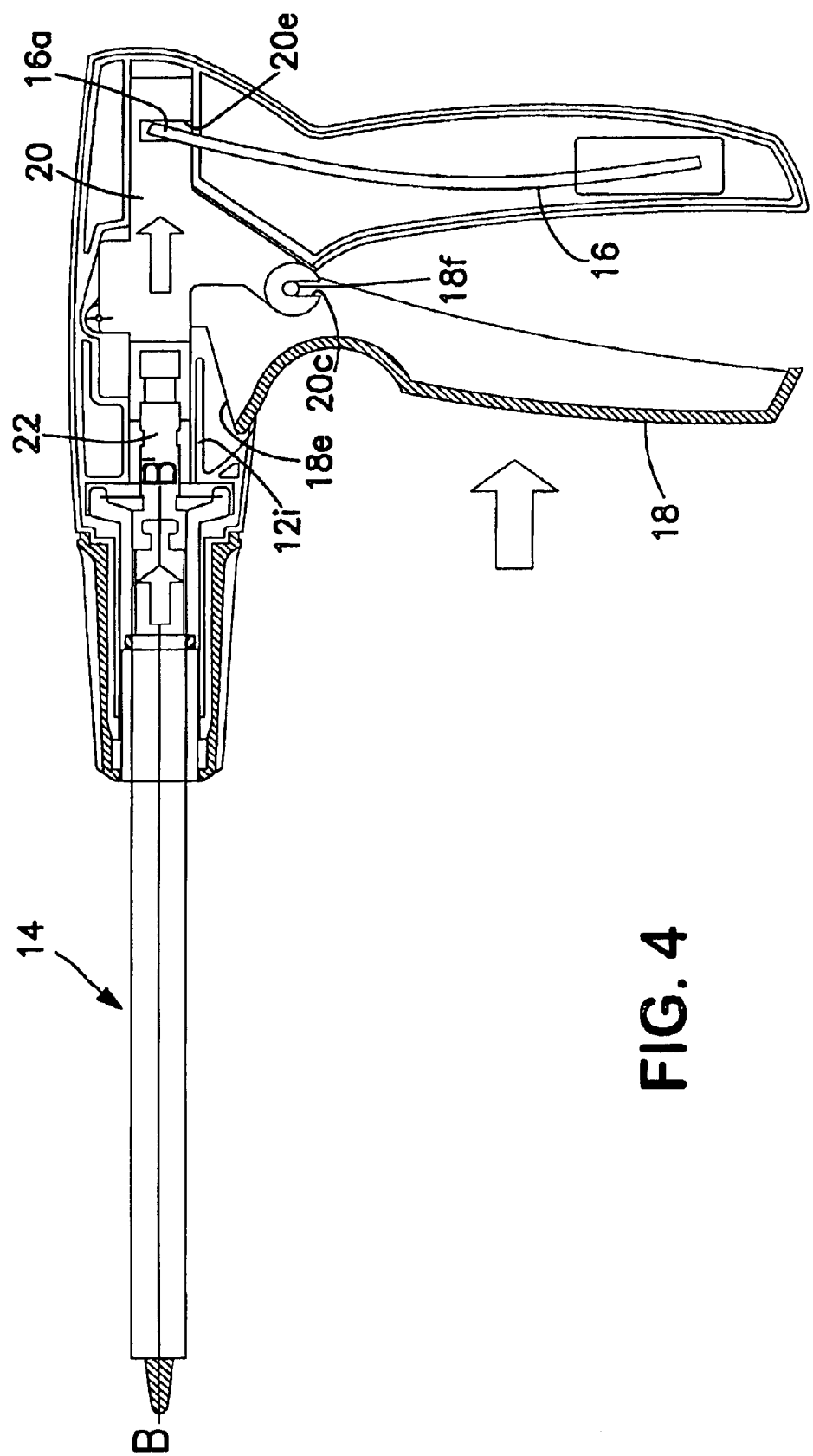
FIG. 4 is a side elevation view of the applicator of FIG. 1 with the operating handle housing partially in section and with handles in pull position.

The rotary drum subassembly 22, 24, 26 comprises the rotary translator 22 positioned axially within the drum 26 with knobs 22k in interior grooves 26b. An anti-backup disc 24 (FIGS. 2, 3 and 7), defined by an open center 24a and slots extending radially from the center to define a plurality of inwardly directed spring fingers 24c, fits onto the rotary translator 22 and is assembled to the enlarged rear end flange 26h of the rotary drum by means of a drum cap 26i. In normal position of the clip applicator with the trigger released, the anti-backup spring fingers 24c are located in the rear anti-backup groove as shown in FIG. 3.

This rotary drum subassembly is then assembled into the forward chamber 12g of the operating handle housing with drum cap 26i fitted into chamber recess 12n (FIG. 2), with the drum front end flange 26g abutting a front rim of the front chamber, and with the rear flange 22b of the rotatable translator positioned within the cage 20f of the fixed translator.

A thumb wheel hub 28 (FIGS. 2, 3, and 8) with cylindrical interior surface 28a, tapered fluted exterior 28b, and front end retaining lip 28c fits over the handle front chamber 12f in abutment with housing exterior shoulder 12k and in abutment with the rotary drum front flange 26g.

The rotary drum subassembly within the operating handle housing is now ready to receive the removable clip cartridge and to impart both reciprocating rectilinear movement to the cartridge and to accommodate rotary movement of the cartridge.

The operation of the anti-backup mechanism is illustrated in FIGS. 9a–g.

As pointed out above, the center section 22c of the rotary translator shaft has spaced anti-backup grooves 22d, 22e with the distance between the grooves being approximately equal to the distance of reciprocating rectilinear motion of the fixed translator and equal to the rectilinear excursion of the clip applicator mechanism.

In the mechanism position of FIGS. 3 and 9a, the handle trigger 18 is in released position with the anti-backup disc 24 in registry with the rear anti-backup groove 22d of the rotary translator 22. When the trigger is pulled (FIG. 4) (for crimping and applying a clip at a surgical site), the rotary translator moves in the direction of arrow 9a. As the rotary translator continues movement, the spring fingers 24c of the disc engage the outer surface 22c of the rotary translator in the manner shown in FIGS. 9b–c. The anti-backup mechanism applied by the canted spring fingers 24c (FIGS. 9b–c) to the outer surface 22c of the rotary translator permits continued movement in the direction of arrow 9a and prevents movement in the opposite direction of arrow 9b. If a surgeon releases the trigger with less than a full pull stroke leaving anti-backup components in the position of FIG. 9c, for example, the anti-backup mechanism holds the rotary translator in position against the bias of bar spring 16 which tends to return the trigger to release position. In this FIG. 9c hold position, the applicator jaws retain the partially crimped clip preventing it from falling into a surgical site. A continuing pull of the trigger (in direction of arrow 9a) moves the rotary translator through the position of FIG. 9c to the position of FIG. 9d in which the spring fingers 24c enter the forward groove 22e.

In this position (FIG. 9d), the rotary translator may now be moved forward (by releasing the trigger and by force of return spring 16) in the direction of arrow 9c. In this forward movement, the spring fingers 24c are effective to allow continued forward movement while preventing movement in the direction of arrow 9e. If the handle trigger is held by a surgeon with components as in FIG. 9f, the anti-backup mechanism will prevent the surgeon from pulling the trigger in the direction of arrow 9e. The surgeon must allow full release of the trigger to component position of FIG. 9g. Direction of movement can be changed again when the spring fingers 24c enter the rear groove 22e as in FIG. 9g.

The clip cartridge 14 (FIGS. 10a–c) includes a tube 14b with its handle end having radially projecting positioning pins 14c emerging from end slots 14d (FIG. 11) in the tube, and an end 14e (FIG. 12) slot for passing the end of a puller bar 30 while maintaining radial alignment of the pins and puller bar. The puller bar terminates in a T shape flange 30a.

Referring to FIGS. 2, 5, 6 and 10a–c, for assembly of clip cartridge 14 and operating handle 12:
(a) the clip cartridge 14 is inserted through keyhole 26j into the front end of the rotary drum 26 with cartridge positioning pins 14c entering interior drum slots 26b;
(b) the T flange 30a projecting through cartridge end slot is in fixed radial orientation in relation to the positioning pins 14c;
(c) the T flange approaches end face 22m of the rotary translator with the T flange in axial registry with the keyhole 22h in the front face of cage flange 22f (FIG. 2);
(d) the T flange passes through the keyhole 22h into the rotary translator cage 22f; and
(e) the cartridge is rotated (arrow 10a) on B–B' axis with cartridge pins 14c entering radial drum slots 26d, 26e (FIG. 6) and the T flange coming to rest against the rotary translator interior cage shoulders 22i (FIG. 5).

The slot spring 26f (FIG. 2) engages one of the pins 14c to hold the clip cartridge in assembled position with the handle.

The cartridge and operating handle are taken apart by reversing the assembly sequence.

Figure 10A:
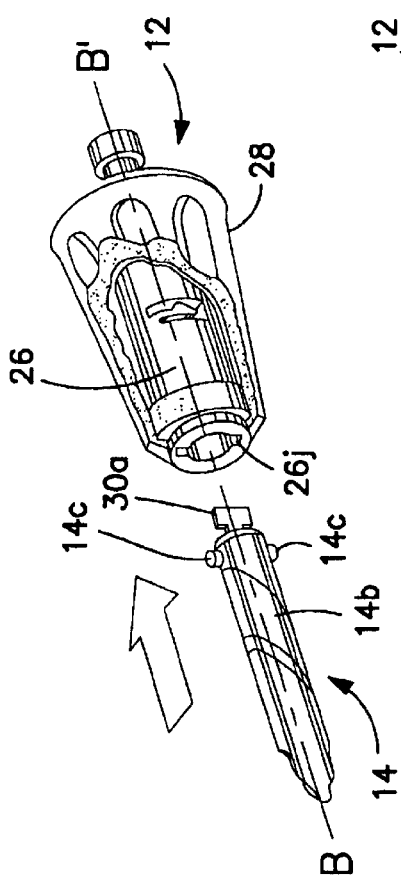
FIGS. 10a, b and c are fragmentary perspective views of the sequence for inserting a clip applying cartridge magazine into a handle assembly housing.
Figure 10B:
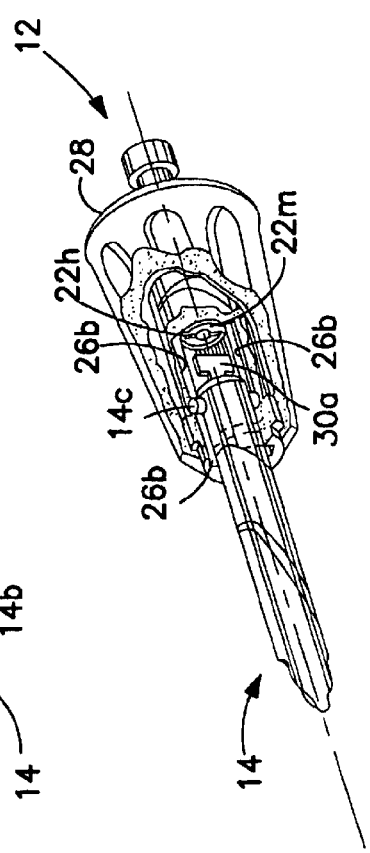
Figure 10C:
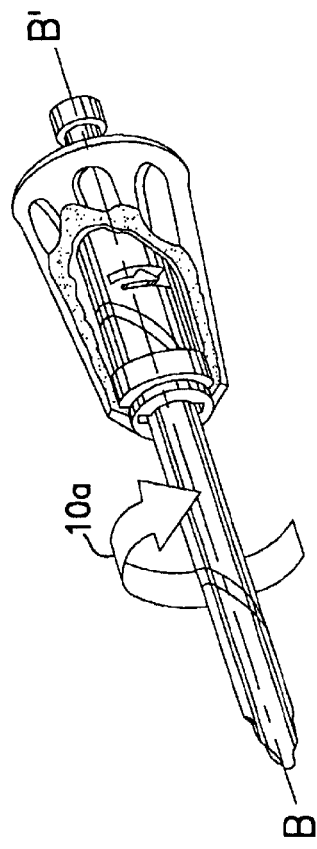

In this clip applier assembly FIGS. 10a–c, the operating handle housing 12 may be considered stationary. The rotary drum subassembly (rotary translator 22, anti-backup mechanism 24 and rotary drum) together with thumb wheel hub 28 and the clip cartridge 14 are rotatable about the B–B' axis by manual application of torque to the thumb wheel and with the rear flange 22b of the rotary translator rotating freely in fixed translator cage 20f. In this way the cartridge is rotatable clockwise and counterclock wise as desired.

A pull on the trigger against the force of bar spring produces unitary rearward rectilinear movement of the fixed translator, the rotary translator passing through the stationary spring fingers of the anti-backup disc, and the puller bar emerging from within the cartridge casing until the trigger and fixed translator reach the end of travel and with the anti-backup disc spring fingers positioned at the front groove. The rearward excursion is now complete, and when the trigger is released, the bar spring urges the fixed translator forward until all components reach normal position.

In the event a pull on the trigger is released without reaching the full extent of rectilinear motion, the anti-back up spring fingers will not have reached their front groove remaining instead in contact with the outer surface of the rotary translator. The spring fingers in contact with outer surface function as a brake against the action of the bar spring tending to force the released components to return to normal position. In this partial pull condition of the trigger a clip has been crimped in the instrument jaws which clip will fall out of the jaws into a surgical site if the jaws reopen by return of the mechanism to normal position. So the anti-backup mechanism retains the instrument in "partial pull position" against the normalizing force of the bar spring and most importantly prevents fallout from the jaws of a partially crimped clip. The anti-backup device retaining action is removed simply by means of a full pull on the trigger causing the spring fingers to enter the forward groove where they can go "over center" thereafter permitting the rotary translator to pass through the spring fingers. It is to be noted that the anti-backup mechanism is effective in both directions. The anti-backup mechanism has effect when the trigger is released after a full pull so that if there is a "partial release" of the trigger, the trigger must nonetheless return to normal position with full release of the trigger before allowing the trigger to be pulled. The design requirement for full release achieved by the anti-backup mechanism prevents double loading of clips into cartridge jaws.

It is a further aspect of the anti-backup mechanism that the cartridge may be rotated on the B–B' axis as the anti-backup mechanism holds the instrument in partial pull position enabling a surgeon to adjust cartridge or jaw position even after a partial pull has occurred.

The clip cartridge 14 FIGS. 11–14a–e comprises an applicator housing tube 32, upper cartridge shell 34 and lower cartridge shell 36 connected to the operating handle housing as described above. The applicator housing upper 34 and lower 36 shells are elongate open ended channels having locating pins 14c serving to connect the cartridge to the handle as described above. The channels together define the end slot 14e (FIG. 12) through which the puller bar end 30a extends into the operating handle. The clip applicator housing encloses and forms part of a clip applicator mechanism 14a. In the following description, the applicator housing upper and lower shells 34, 36 are regarded as stationary in relation to movement of the applicator mechanism components.

The lower cartridge shell 36 has an anchor pin 36a affixed to the channel base interior 36b. The lower cartridge shell receives a cam puller bar 38 and coil spring 38a for sliding movement, and clip applicator jaws 40 mounted on the anchor pin 36a. The cartridge puller bar 30 overlies the cam puller bar 38.

The elongate cartridge puller bar 30 is located in the applicator lower shell 36c with the bar connected at its T shape rear end 30a to the rotary translator for receiving linear reciprocating motion with respect to the stationary lower shell 36 for each cycle of the handle operating trigger. The cartridge puller bar toward its front end includes laterally extending tabs 30b which cooperate with the cam puller bar 38. The cartridge puller bar also has a round hole 30c for receiving a magazine pin 42a depending from the underside of a clip magazine 42 by which the cartridge puller bar actuates the clip magazine. The magazine pin also passes through an elongate slot in a stationary clip plate 41.

The cam puller 38 occupies the lower shell beneath the cartridge puller bar and the clip applicator jaws. The cam puller bar is fitted with upstanding cooperating cam members 38b for closing and opening the clip applicator jaws 40. The cam puller bar includes a rear tang 38c and coil spring 38a accommodated in a recess 36b in the lower shell. The cam puller further includes an anchor pin slot 38d to accommodate reciprocal movement of the cam puller past the anchor pin 36a in the base channel and a cartridge pin slot 38e for accommodating movement of the cam puller past the cartridge pin 42a fitted to the underside of the clip supply magazine. The cam puller is fitted with spaced sets of upwardly extending tabs 38f and 38g for cooperating with the cartridge puller bar lateral tabs 30b.

So, the cam puller 38 is urged by coil spring 38a toward the foward end (i.e., the jaws end) of the clip cartridge so as to leave the clip applicator jaws 40 normally open. The cartridge puller bar 30 is normally forward under the influence of the handle bar spring with puller tabs 30b abutting the forward set of cam puller tabs 38f. When the trigger handle is pulled (FIG. 12a), the cartridge puller bar 30 moves rearward (with lost motion or dwell between cam puller bar forward 38f and rear 38g tab sets) until the cartridge puller tabs 30b engage the rear set 38g of cam puller tabs thereby drawing the cam puller 38 to the rear against its coil spring for closing the applicator jaws. The cartridge pin slot 38e accommodates cam puller movement past the cartridge channel pin 42a during the time of lost motion between the cartridge puller bar 30 and cam puller tab sets 38f–g.

Lost motion of the cam puller bar ensures that the applicator jaws remain open for a portion of the rearward movement of the cartridge puller bar before the jaws close and crimp a clip in surgery. It is desirable to crimp the clip at the end of rearward travel so as to provide the surgeon with a natural feel for releasing the handle. Lost motion also has significance on the forward stroke of the clip applicator mechanism by ensuring the applicator jaws are open to receive a clip during the forward stroke of the applicator mechanism, as is to be fully understood with description of the clip supply magazine and associated mechanisms below.

Clip applying jaws 40 comprising spring biased arms 40c–d are mounted at opening 40e to anchor pin 36a on the applicator lower shell with the jaws projecting from the front end of the base channel.

Figure 11:
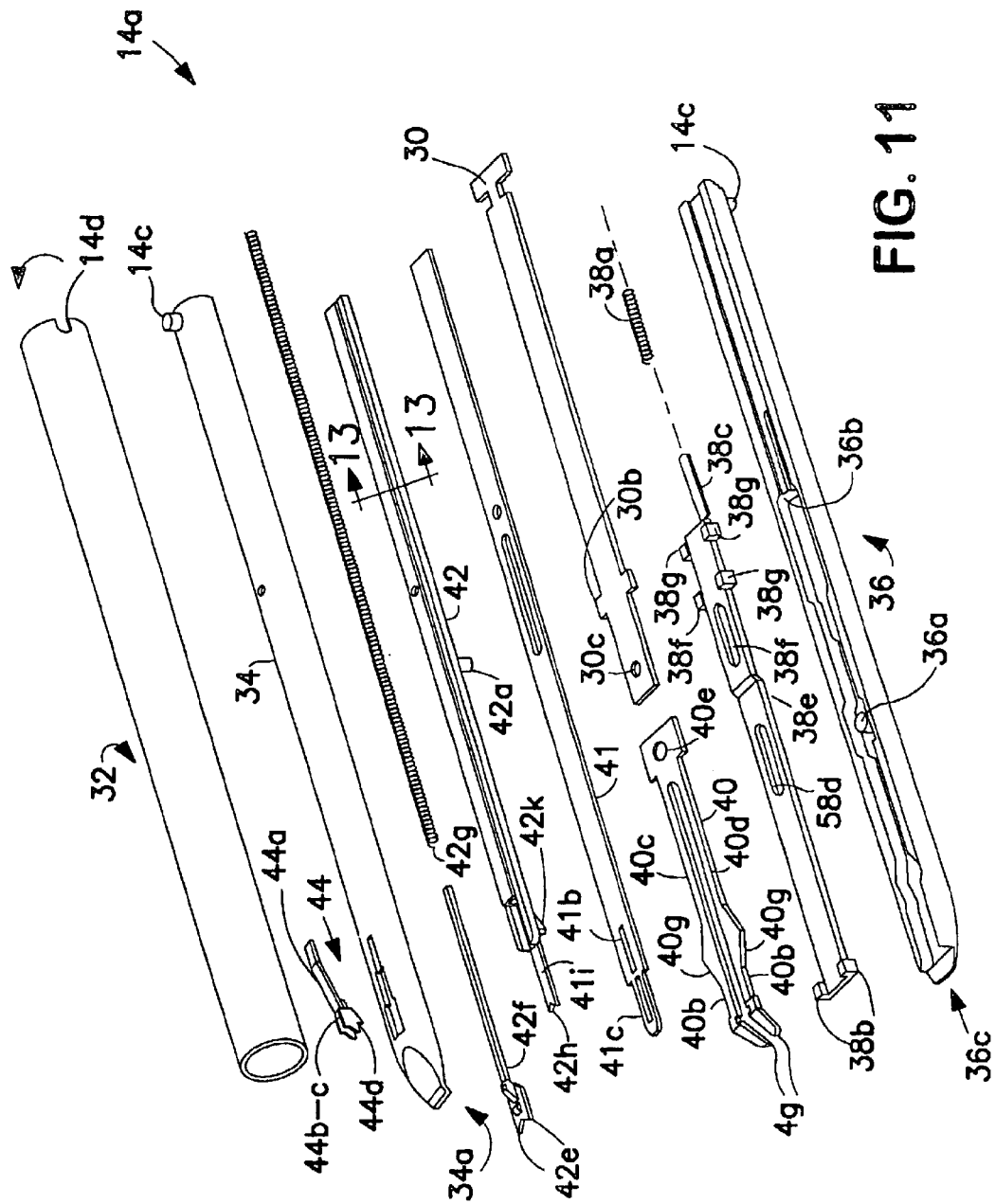
FIG. 11 is a perspective view of individual cartridge mechanism components.
Figure 12B:
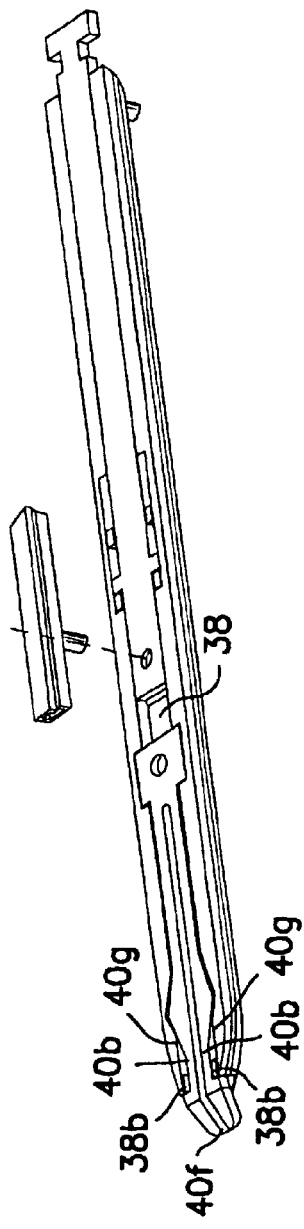
FIGS. 12a–b are sequential fragmentary perspective views of puller bar/cam puller "lost motion" with related cartridge components.
Figure 12A:
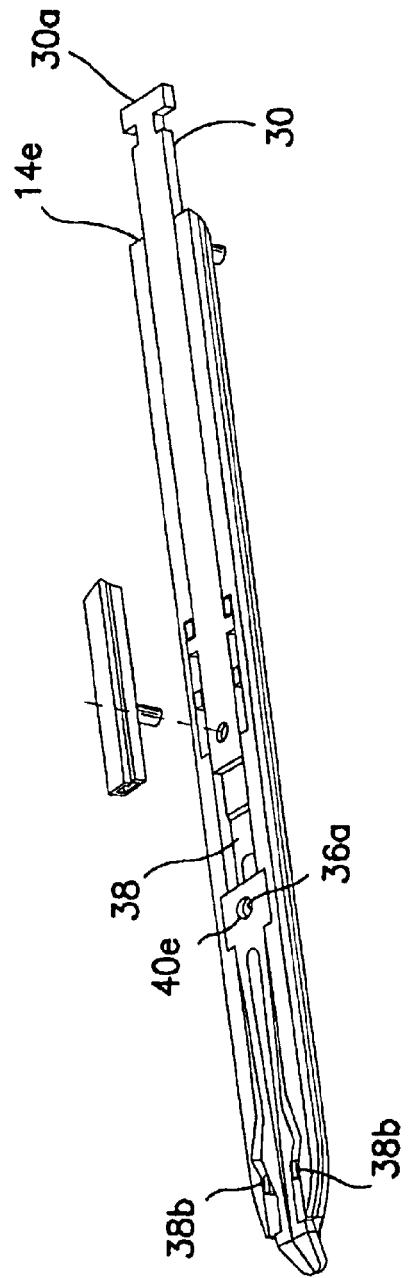
Figure 13:
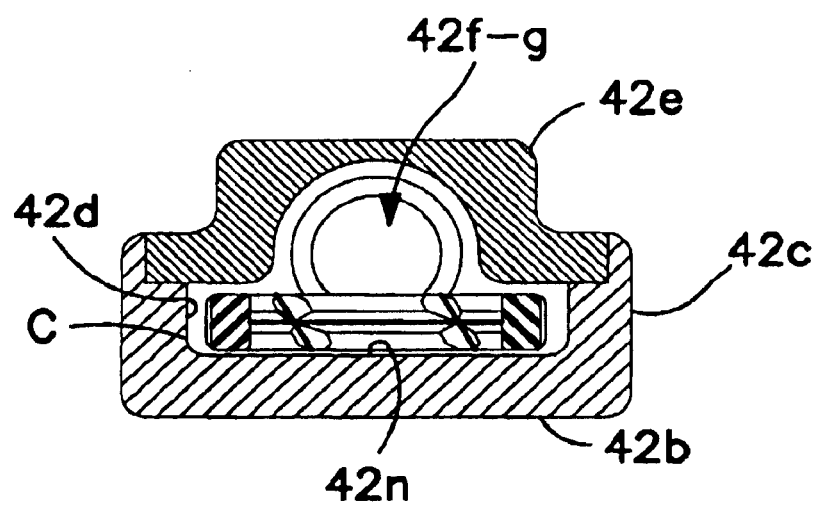
FIG. 13 is an enlarged section view taken along line 13—13 of FIG. 11.
Figure 15A:
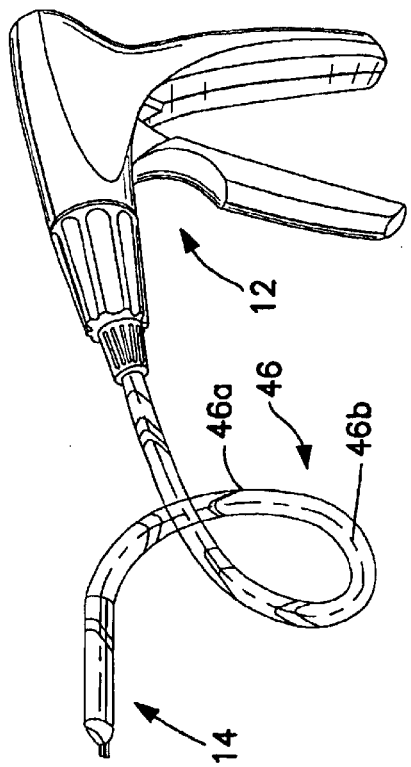
FIGS. 15a and b are perspective views of a repeating multi-clip applier according to the invention having a flexible shaft interposed between cartridge and pistol grip handle.
Figure 15B:
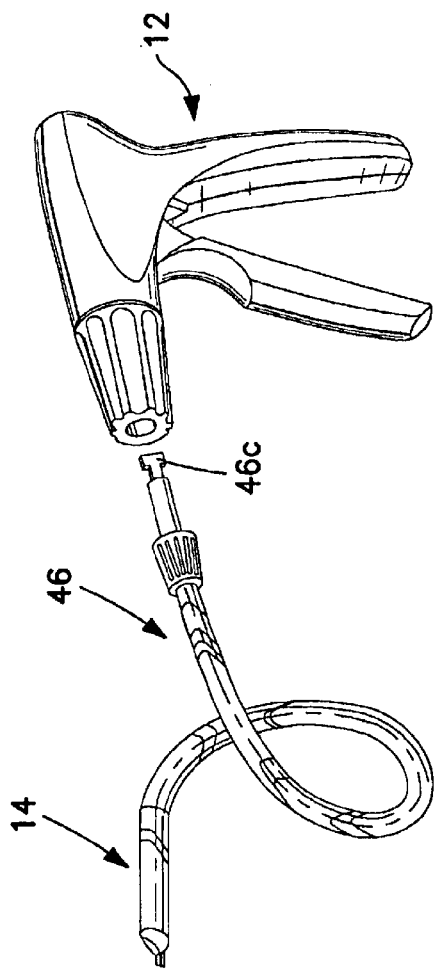
Figure 16A:
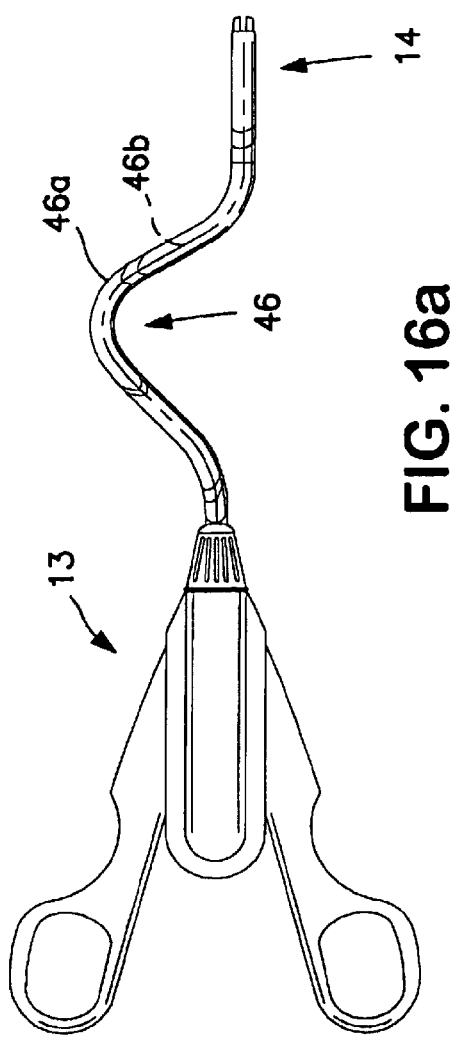
FIGS. 16a and b are perspective views of a repeating multi-clip applier according to the invention having a flexible shaft interposed between cartridge and scissors operating handle.
Figure 16B:
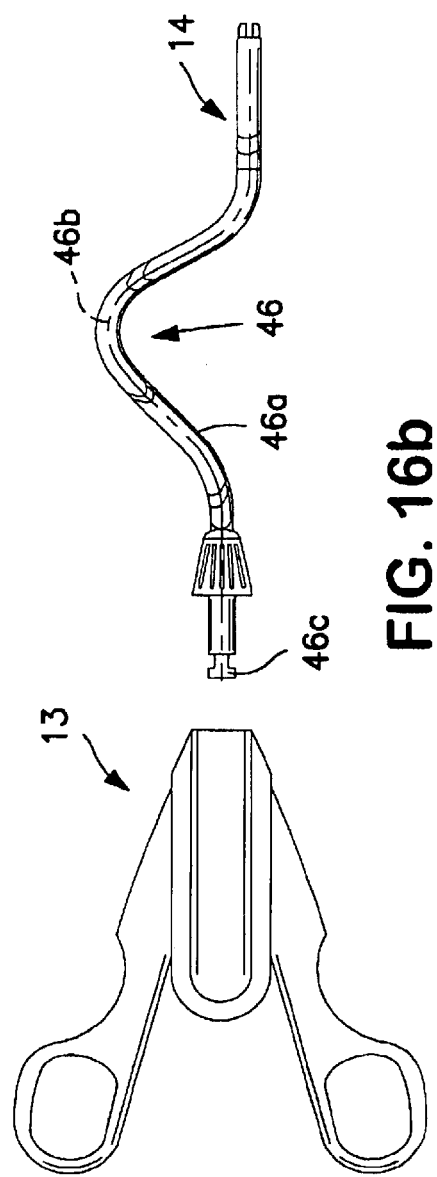

FIGS. 11 and 12a–b illustrate spring biased applicator jaws affixed to the applicator housing anchor pin 36a with spring biased arms 40c–d able to move from open-to-closed-to-open positions in applying a clip. The inner surfaces 40f of the jaws are recessed to form cooperating channels for movement of each clip into the jaws. The outer surfaces of the jaws have aligned recesses 40b and inclined cam surfaces 40g cooperating with aligned cam members 38b affixed to the cam puller for the purpose of closing the jaws for each rearward excursion of the cartridge puller bar 30. The jaws are released to spring open on the forward excursion of the cam puller placing the cam members within the recesses 40b. The normal position for the cam puller 38 and jaws 40 occurs with the cam puller at the forward end of linear excursion, with the jaws open and with the cam puller cam members 38b in an inactive position with respect to applicator jaws as in FIG. 12b.

The cartridge applicator mechanism includes a clip supply magazine 42 (FIGS. 11, 13 and 14a–e) which is affixed to and reciprocates with the cartridge puller bar 30 by means of magazine pin 42a at the underside the magazine fitting into hole in the puller bar. The clip supply magazine and cartridge puller bar are separated by a stationary clip plate 41 having a central slot 41a to accommodate sliding movement of the clip supply magazine 42 and its pin 42a by means of the cartridge puller bar. The clip plate 41 includes a cam slot 41b and front end clip ramp 41c cooperating with the clip supply channel as described below.

The clip supply magazine 42 (FIGS. 11, 13) includes an elongate base plate 42b with upstanding sides 42c to define a central channel 42d for receiving and retaining a line of clips C. A dome 42e extends between the sides for receiving an elongate clip follower 42f and coil spring 42g. The clip follower is positioned and retained in the clip supply magazine in engagement with the last clip $C_Z$ (FIG. 14) and is urged forward by the coil spring for advancing the line of clips along the supply channel. The clip follower has forwardly directed fingers 42h for engaging clip shoulders for constantly maintaining a force on the line of clips by means of the coil spring.

The clip supply magazine 42 (FIG. 11) has an integral forwardly extending pusher plate 42i preferably with notched front edge 42h conforming to clip contour for the purpose of pushing each clip into the jaws as it leaves the supply magazine.

A clip stop spring 42k (FIGS. 11, 14) with vertical tip 42m is formed integral in the base plate 42b of the clip magazine for gripping the leading clip $C_L$ at midpoint. The clip stop spring has a "spring set" wherein the spring is normally positioned or biased below the surface 42n of base plate (as in FIG. 14a) with the spring being accommodated in the cam slot 41b (FIGS. 11 and 14) of stationary clip plate 41 located underneath the magazine.

The clip plate 41 is fixed to the stationary housing by suitable means so that the back edge of the cam slot 41b urges the clip stop spring 42k and its tip upward into the path of clips C when the clip magazine moves rearward with the cartridge puller bar (FIGS. 14a–c). As noted above, the slot 41a in the clip plate accommodates reciprocal movement of the clip magazine/puller bar connecting pin 42a.

The housing upper shell 34 has depending from its inner surface a clip detent spring 44 (FIGS. 11, 14) and a guide ramp surface 34a for positioning clips for movement into clip applying jaws. The clip detent spring comprises a leaf spring 44a with spaced depending panels 44b–c of identical edge contour terminating in forwardly directed notches 44d for engaging the shoulders of a lead clip $C_L$ to separate the lead clip from the line as the line of clips and the clip magazine are pulled rearward by clip stop spring 44k and cartridge puller bar 30 with a pull of the operating trigger. On release of the trigger and consequent forward movement of the clip magazine (FIGS. 14d–e), the cartridge pusher plate 42i engages the rear surface of the detained lead clip $C_L$ and pushes it into the crimping jaws.

The action of clip moving components is shown in FIGS. 14a–e starting with FIG. 14a which shows components in forward position and a clip $C_J$ in the instrument jaws.

Referring to FIG. 14a, a first in line of clips $C_F$ is at rest under the detent spring notches 44d for the purpose of separating clip $C_F$. The detent spring 44 is stationary in that it is affixed to the under side of the housing cover in position to capture and hold the lead clip $C_F$ at the end of the forward excursion of the cartridge puller bar and clip supply magazine. The detent spring takes and separates the lead clip $C_F$ from the clip line in preparation for movement of the lead clip into the applicator jaws on a subsequent applicator cycle. The detent spring separates clip $C_F$ by reaction as the inclined rear edges ride up (FIG. 14e) on forwardly moving clip $C_F$ and snap down (FIG. 14a) as the clip passes the shoulders. Such clip capture occurs as the puller bar and clip magazine reciprocate during operation of the applicator, as detailed below.

From the position of FIG. 14a, a rearward pull of the trigger begins immediate rearward sliding movement of clip supply magazine 42 with respect to stationary upper shell 42 and stationary clip plate 41. The clip detent spring 44 holds and separates clip $C_F$ from the line of clips. The line of clips moves rearward with the clip cartridge as clip stop spring 42k is cammed upward (FIG. 14b) by cam slot 41b in clip plate 41. As movement continues (FIG. 14c), the cartridge pusher plate 42i also moves rearward sliding underneath clip $C_F$ and coming to rest behind the clip (FIG. 14d) at the end of the rearward stroke of the operating handles. As pusher plate 42i slides behind clip $C_F$, the clip detent spring 44 (having a normal downward spring force) pushes clip $C_F$ downward into contact with clip ramp 41c. When the operating handles are released, beginning from the position of FIG. 14d and continuing to FIG. 14e, the clip cartridge pusher plate 42i engages clip $C_F$, pushes it forward between upper shell ramp surface 34a and clip plate ramp 41c and on into the instrument jaws. As this forward motion occurs, the clip detent spring 44 rides up on clip $C_L$ with notches 44d coming to rest behind the clip shoulder as illustrated in FIG. 14a.

The operation of the clip applicator is as follows. The housing upper and lower shells are stationary with respect to movements of the component parts of the actuating mechanism. At the beginning of an operating cycle (or normal position), the handle trigger is in forward or release position, the cartridge puller bar and clip supply magazine are in forward position, the jaws are open holding a clip in position for surgical application, jaw actuating cam puller means are in inactive position, the lead clip in the capture position under clip detent spring, the cartridge pusher plate lies under the captured lead clip, the clip stop spring is inactive and lies in the clip plate cam slot below the surface of the pusher plate, the spring loaded clip follower engages the last in line clip, and the spring biased line of clips is in contact with lead clip $C_F$.

By squeezing the trigger, the puller bar and clip magazine move rearward relative to the stationary upper and lower shells and stationary clip plate to accomplish:

a. movement of the magazine pusher plate out of the jaws,
b. continued movement of the pusher plate relative to the clip plate whereby the stop spring is cammed up so its tip grips the next in line clip $C_L$ and by continued rearward movement the stop spring separates the clip stack from the lead clip $C_F$;
c. after an initial lost motion or dwell phase during which the jaws are open, engagement of cartridge puller bar tabs and cam puller tabs for pulling cams means along jaw cam surfaces to close the jaws and crimp a clip in surgical application,
d. the captured clip $C_F$ is held in place under the clip detent spring;
e. movement of the cartridge pusher plate from underneath captured clip $C_F$ into position behind clip $C_F$;
f. downward movement of clip detent spring and clip $C_F$ on to the clip plate ramp and in front of the clip pusher plate;

and by releasing the trigger, the cartridge puller bar and clip supply magazine move forward in relative movement to the stationary upper and lower shells and stationary clip plate to accomplish:

g. disengagement of the cartridge puller bar tabs from the cam puller tabs and forward movement of the cam puller bar under the influence of its coil spring thereby moving cam means along the jaws cam surfaces into inactive position thereby opening the jaws;
h. movement of the cartridge pusher plate to advance the captured clip $C_F$ into the jaws; and
i. the cartridge pusher plate and stop spring move relative to the clip plate with the stop spring reentering its slot in the clip plate out of the path of the clip line so as to permit the next in line clip $C_L$ to advance along the surface of the pusher plate to deflect the clip detent spring and be captured as $C_F$.

The invention provides that the clip applicator of FIG. 2 of the drawing can be made as a disposable cartridge to be inserted into a non-disposable handle with the cartridge removed from the handle and discarded after its clips are consumed. In a cartridge arrangement both the cartridge housing and rear end of the actuating rod have plug-in connections to the handle housing and link journal respectively.

In accordance with the invention, the magazine pusher plate acts as a lock-out of the jaws after all the clips in the cartridge magazine have been used and there are none left. Such lock-out action occurs as the pusher plate without a clip to push itself enters the space between the crimping jaws and prevents the jaws from closing thereby indicating to the surgeon that there are no more clips to be applied.

The clip applying mechanism of the invention may include a flexible shaft interposed between operating handle and clip cartridge. As shown in FIGS. 15a–b and 16a–b, a flexible shaft 46 comprising a sheath 46a, interior flexible wire 46b, and T-shape end 46c interconnects operating handle 12 in the form of a pistol grip and in the form of a scissor 13 with the clip applying cartridge 14. The flexible shaft 46 is capable of bending as desired up to 360° with respect to its handle as the clip cartridge maintains full operational clip applying integrity.

A clip applicator according to the invention has a simplified construction and low cost of manufacture at high production rates, low operating force without recoil, a clip counter, jaw lockout after the last clip, an anti-backup mechanism, a 360° rotatable clip cartridge, and is adaptable for use as a quick snap-in disposable cartridge with a fixed non-disposable operating handle. An operating handle that provides linear reciprocating motion including scissors-type, pistol grip, and surgical robot may be used in the invention. The applicator according to the invention is adaptable for use with surgical clips in a range of sizes.

Various changes may be made to the structure embodying the principles of the invention. The foregoing embodiments are set forth in an illustrative and not in a limiting sense. The scope of the invention is defined by the claims appended hereto.

I claim:

1. An operating handle for a cartridge to apply clips in surgery, the operating handle comprising a housing defining an interior chamber for receiving operating components, the handle having actuating means for providing linear movement to the operating components, the operating components comprising:
    a. first means for receiving from the actuating means reciprocal linear motion of predetermined excursion,
    b. second means connected to said first means for rotation about an axis and for receiving linear motion from the first means, and
    c. third means cooperating with the second means for receiving a cartridge and linking the cartridge to the second means to impart reciprocal motion to the cartridge and to accommodate rotary motion of the cartridge about said axis.

2. An operating handle for a cartridge having a clip applying mechanism to apply clips in surgery, the operating handle comprising a pistol grip housing having a trigger, the housing defining an interior chamber for receiving operating components, the trigger mounted on the housing for reciprocal movement, means for urging the trigger to a normal position, the operating components comprising:
    a. first means for receiving from the trigger reciprocal linear motion of predetermined excursion defined by first and second strokes,
    b. second means connected to said first means for rotation about an axis and for receiving linear motion from the first means,
    c. third means in assembly with the second means and cooperating with the second means for receiving a cartridge and for imparting linear motion to the cartridge mechanism and for accommodating of the cartridge about said axis, and
    d. anti-backup means constraining the second means to complete the excursion of one of said first and second strokes before beginning the other of said first and second strokes.

3. An operating handle for a cartridge to apply clips in surgery, the operating handle comprising a pistol grip housing having a trigger, the housing defining an interior chamber for receiving operating components, the trigger mounted on the housing for reciprocal movement, means for urging the trigger to a normal position, the operating components comprising:
    a. first means for receiving from the trigger reciprocal inear motion of predetermined excursion defined by first and second strokes,
    b. second means connected to said first means for rotation about an axis and for receiving linear motion from the first means,
    c. anti-backup means constraining the second means to complete the excursion of one of said first and second strokes before beginning the other of said first and second strokes, and
    d. means in subassembly with the second means for mounting a cartridge to the operating handle whereby the operating components provide linear reciprocating motion of predetermined excursion to the cartridge and accommodate rotation of the cartridge about said axis.

4. An operating handle for a cartridge to apply clips in surgery, the operating handle comprising a pistol grip housing having a trigger, the housing defining an interior chamber for receiving operating components arranged along a longitudinal axis, the trigger mounted on the housing for reciprocal movement, means for urging the trigger to a normal position, the operating components comprising:
    a. a fixed translator slidably mounted in the housing for reciprocal linear motion of predetermined excursion defined by first and second strokes, the fixed translator linked to the trigger for movement through said excursion,
    b. a rotary translator connected to the fixed translator for rotation about said axis and for receiving linear motion from the fixed translator, the rotary translator having first and second means spaced from each other a distance approximately equal to said excursion,
    c. anti-backup means cooperating with the rotary translator first and second means for constraining the the rotary translator to complete the excursion of one of said first and second strokes before beginning the other of said first and second strokes, and
    d. a rotary drum in subassembly with the rotary translator for releasably mounting a cartridge to the operating handle whereby the operating components provide linear reciprocating motion of predetermined excursion to the cartridge and accommodate rotation of the cartridge about said axis.

5. In a clip applying instrument having a clip applying cartridge and having an operating handle with operating components for generating reciprocal linear motion of fixed excursion defined by forward and reverse strokes along an axis and for imparting said linear motion to said cartridge, the improvement comprising a rotary drum subassembly forming part of the operating components and having:
    a. a rotary drum having an interior chamber and mounted with said handle for rotary motion about said axis,
    b. a rotary translator assembled with the rotary drum for rotation with the rotary drum and for linear movement with the operating components through the strokes of said fixed excursion,
    c. the rotary translator having first and second means defining the limits of the fixed excursion, and
    d. an anti-backup mechanism in assembly with the rotary drum and cooperating with the rotary translator first and second means to ensure the forward and reverse strokes of linear excursion of the rotary translator are completed without backup movement of the operating components.

6. An anti-backup mechanism for a device having liner reciprocating motion through forward and reverse strokes, the anti-backup mechanism comprising a drum, a translator assembled with the drum for linear reciprocating movement through said strokes, the translator having first and second means defining the limits of reciprocating motion, and an anti-backup disc mounted on the drum and cooperating with the translator first and second means to ensure the forward and reverse strokes of linear excursion of the translator are completed without backup movement.

7. An operating handle for a clip applying cartridge having a cartridge puller bar with a rear connecting end comprising:
    i. a pistol grip housing defining a chamber for receiving operating components and having a trigger for imparting to the operating components linear reciprocating motion of fixed excursion consisting of forward and reverse strokes, and a spring for urging the operating components in a direction of linear motion, ii. operating components arranged on a longitudinal axis including:
   a. a fixed translator for receiving said linear motion from the trigger and the urging of said spring, the fixed translator having a cage for receiving a rotary translator,
   b. a rotary translator fitted to said cage for linear motion with the fixed translator and for rotary motion on said longitudinal axis, the rotary translator having an elongate body and an open, front end cage for receiving the rear connecting end of the cartridge puller bar, the rotary translator having spaced grooves on its surface a distance approximately equal to the fixed excursion,
   c. an anti-backup in the form of a disc with inwardly directed spring fingers terminating at a central aperture in the disc,
   d. a rotary front and rear open-ended drum in subassembly with the rotary translator and anti-backup disc with the rotary translator positioned axially within the rotary drum for linear motion with respect to the rotary drum and with the rotary translator passing through the central aperture of the anti-backup disc, the disc cooperating with the spaced grooves of the rotary translator to provide an anti-backup mechanism in the operating components, the rotary drum open front end for receiving and passing the cartridge puller bar rear connecting end for engagement with the front end cage of the rotary translator,
   e. whereby the operating components transmit said linear motion to the clip applying cartridge, constrain said linear motion to complete forward and reverse strokes without backup, and accommodate rotary motion of the clip applying cartridge with respect to longitudinal axis.

8. A clip applying cartridge comprising a housing for receiving a clip applying mechanism, the clip applying mechanism comprising:
   a. clip applying jaws secured to the housing for receiving and applying clips,
   b. cam means for closing the jaws to apply a clip and for releasing the jaws so the jaws open to receive another clip,
   c. puller means providing linear reciprocating movement to clip applying mechanism components, the puller means cooperating with the cam means for closing and opening the jaws,
   d. a clip supply magazine containing a line of clips including a first in line clip to be applied by the mechanism, having means for pushing a clip into the jaws, having means for urging the line of clips toward the jaws, having means for retracting the line of clips, and being connected to the puller means to receive linear reciprocating movement, and
   e. clip detent means for engaging and moving a first in line clip into position for the clip pusher means to push said clip into the jaws.

9. A clip applying cartridge comprising a housing for receiving a clip applying mechanism, the clip applying mechanism comprising:
   a. clip applying jaws secured to the housing for receiving and applying clips,
   b. cam means for closing the jaws to apply a clip and for releasing the jaws so the jaws open to receive another clip,
   c. puller means providing linear reciprocating movement of first and second strokes to clip applying mechanism components, the puller means cooperating with the cam means for closing and opening the jaws,
   d. a clip supply magazine containing a line of clips including a first in line clip to be applied by the mechanism, having a pusher plate for pushing a clip into the jaws, having means for urging the line of clips toward the pusher plate, having a means for engaging and retracting the line of clips except the first in line clip, and being connected to the puller means to receive linear reciprocating movement, and
   e. clip detent means for engaging and moving the first in line clip into position for the pusher plate,
   whereby a first stroke of the puller means actuates the clip applying mechanism to close the jaws to apply a clip, to engage and retract the line of clips except the first in line clip, to move the first in line clip into position for the pusher plate, and a second stroke of the puller means actuates the clip applying mechanism to open the jaws, to push the first in line clip into the jaws, to advance the line of clips from retracted position, and to capture the next first in line of the advanced line of clips.

10. A clip applying cartridge as defined in claim 9 in which the clip applying jaws are affixed to the housing and have cooperating arms with cooperating jaw heads and cam surfaces engaged by the cam means by which the jaws close and are released for opening.

11. A clip applying cartridge as defined in claim 9 in which the cam means is slidably mounted for reciprocal linear movement in the housing, has cam means for closing and releasing the jaws, is spring biased for normally releasing the jaws, and is linked to the puller means to receive linear reciprocating motion.

12. A clip applying cartridge as defined in claim 11 in which the cam means is linked to the puller means to delay closing of the jaws on the first stroke, and to release the jaws in the course of the second stroke.

13. A clip applying cartridge as defined in claim 9 in which the clip supply magazine is integral with the pusher plate, has is spring loaded clip pusher for urging the line of clips toward the pusher plate, has an integral stop spring for engaging and retracting the line of clips except the first in line clip, and has a pin for connection to the puller means to receive linear reciprocating movement.

14. A clip applying cartridge as defined in claim 9 in which the clip detent means comprises a spring mounted on the housing above the line of clips with spring bias into the path of clip movement, and the clip detent means having spaced depending panels having aligned notches for engaging and capturing a first in line clip.

15. A clip applying instrument comprising:
   A. an operating handle in the form of a pistol grip housing having a trigger, the housing defining an interior chamber for receiving operating components, the trigger mounted on the housing for reciprocal movement, means for urging the trigger to a normal position, the handle operating components including:
      i. first means for receiving from the trigger reciprocal linear motion of predetermined excursion defined by first and second strokes,
      ii. second means connected to said first means for rotation about an axis and for receiving linear motion from the first means, and
      iii. anti-backup means constraining the second means to complete the excursion of one of said first and second strokes before beginning the other of said first and second strokes, B. a clip applying cartridge in the form of a housing for receiving a clip applying mechanism, the clip applying mechanism including:
   i. clip applying jaws secured to the housing for receiving and applying clips,
   ii. cam means for closing the jaws to apply a clip and for releasing the jaws so the jaws open to receive another clip,
   iii. puller means secured to the handle for providing linear reciprocating movement of first and second strokes to clip applying mechanism components, the puller means cooperating with the cam means for closing and opening the jaws,
   iv. a clip supply magazine containing a line of clips including a first in line clip to be applied by the mechanism, having a pusher plate for pushing a clip into the jaws, having means for urging the line of clips toward the pusher plate, having a means for engaging and retracting the line of clips except the first in line clip, and being connected to the puller means to receive linear reciprocating movement, and
   v. clip detent means for engaging and moving the first in line clip into position for the pusher plate,
      whereby a first stroke of the handle actuates the clip applying mechanism to close the jaws to apply a clip, to engage and retract the line of clips except the first in line clip, to move the first in line clip into position for the pusher plate, and a second stroke of the handle actuates the clip applying mechanism to open the jaws, to push the first in line clip into the jaws, to advance the line of clips from retracted position, and to capture the first in line of the advanced line of clips.

16. A clip applying instrument as defined in claim 14 in which a flexible shaft interconnects the operating handle and the clip applying cartridge.

\* \* \* \* \*

UNITED STATES PATENT AND TRADEMARK OFFICE
CERTIFICATE OF CORRECTION

| | | |
|---|---|---|
| PATENT NO. | : 6,869,435 B2 | Page 1 of 1 |
| APPLICATION NO. | : 10/051513 | |
| DATED | : March 22, 2005 | |
| INVENTOR(S) | : Joseph W Blake III | |

It is certified that error appears in the above-identified patent and that said Letters Patent is hereby corrected as shown below:

Title page, item [76] inventor should read -- Joseph W Blake III --.

Signed and Sealed this
Twenty-eighth Day of February, 2012

David J. Kappos
*Director of the United States Patent and Trademark Office*